US011892456B2

United States Patent
Nagai et al.

(10) Patent No.: US 11,892,456 B2
(45) Date of Patent: Feb. 6, 2024

(54) METHOD OF EXAMINING DIABETIC COMPLICATION

(71) Applicants: TOKAI UNIVERSITY EDUCATIONAL SYSTEM, Tokyo (JP); RIKEN, Saitama (JP)

(72) Inventors: Ryoji Nagai, Kumamoto (JP); Naoyuki Taniguchi, Saitama (JP)

(73) Assignees: TOKAI UNIVERSITY EDUCATIONAL SYSTEM, Tokyo (JP); RIKEN, Saitama (JP)

(*) Notice: Subject to any disclaimer, the term of this patent is extended or adjusted under 35 U.S.C. 154(b) by 694 days.

(21) Appl. No.: 16/764,595

(22) PCT Filed: Nov. 16, 2018

(86) PCT No.: PCT/JP2018/042575
§ 371 (c)(1),
(2) Date: May 15, 2020

(87) PCT Pub. No.: WO2019/098351
PCT Pub. Date: May 23, 2019

(65) Prior Publication Data
US 2020/0386765 A1 Dec. 10, 2020

(30) Foreign Application Priority Data
Nov. 17, 2017 (JP) .................. 2017-221846

(51) Int. Cl.
*G01N 33/66* (2006.01)
*G01N 33/68* (2006.01)
(52) U.S. Cl.
CPC ......... *G01N 33/66* (2013.01); *G01N 33/6812* (2013.01); *G01N 2800/042* (2013.01); *G01N 2800/56* (2013.01)

(58) Field of Classification Search
CPC ......... G01N 2800/042; G01N 33/6806; G01N 33/6809; G01N 33/6812
See application file for complete search history.

(56) References Cited

U.S. PATENT DOCUMENTS

2013/0345175 A1  12/2013 Beisswenger

FOREIGN PATENT DOCUMENTS

JP  2004-323515  11/2004
JP  2013-257328  12/2013

OTHER PUBLICATIONS

Ohno, R.-I. et al. "Glucoselysine is derived from fructose and accumulates in the eye lens of diabetic rats," J. Biol. Chem. (2019) 294(46) 17326-17338; Oct. 8, 2019 (Year: 2019).*

(Continued)

*Primary Examiner* — Jennifer Wecker
*Assistant Examiner* — Michelle Adams
(74) *Attorney, Agent, or Firm* — Wenderoth, Lind & Ponack, L.L.P.

(57) ABSTRACT

A marker for examining a diabetic complication comprising a compound represented by the following Formula (1), or a salt thereof. A method of examining a diabetic complication with an amount of the marker as an indicator including: (A) a step of measuring the amount of the marker in a sample collected from a test subject; and (B) a step of determining presence or absence, or a risk of development of the diabetic complication based on a result of measurement of the amount of the marker comprising Formula (1), or a salt thereof:

(Continued)

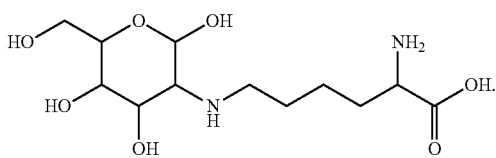

(1)

7 Claims, 6 Drawing Sheets

(56) References Cited

OTHER PUBLICATIONS

Schalkwijk, C.G. et al. "Fructose-mediated non-enzymatic glycation: sweet coupling or bad modification," Diabetes Metab Res Rev 2004; 20: 369-382. (Year: 2004).*

McPherson, J.D. et al. "Role of Fructose in Glycation and Cross-Linking of Proteins," Biochemistry 1988, 27, 1901-1907 (Year: 1988).*

Treibmann, S. et al. "Lysine-Derived Protein-Bound Heyns Compounds in Bakery Products," J. Agric. Food Chem. 2017, 65, 10562-10570. Published Nov. 7, 2017 (Year: 2017).*

International Search Report dated Feb. 19, 2019, in International (PCT) Application No. PCT/JP2018/042575.

Ichimaru et al., "About fructose-modified amino acid in lens of diabetic rat—Isolation, Determination of structure, Detection by LC-MS/MS-", JMARS News Letter, 2018, vol. 17, pp. 1-8, with partial English translation.

Nagai et al., "Detection of AGEs as markers for carbohydrate metabolism and protein denaturation", Journal of Clinical Biochemistry and Nutrition, 2014, vol. 55, No. 1, pp. 1-6.

Reddy et al., "N$^{epsilon}$-(Carboxymethyl)lysine Is a Dominant Advanced Glycation End Product (AGE) Antigen in Tissue Proteins", Biochemistry, 1995, vol. 34, No. 34, pp. 10872-10878.

Nagai et al., "Antibody-based detection of advanced glycation end-products: promises vs. limitations", Glycoconjugate Journal, 2016, vol. 33, No. 4, pp. 545-552.

* cited by examiner

METHOD OF EXAMINING DIABETIC COMPLICATION

TECHNICAL FIELD

The present invention relates to: a marker for a diabetic complication; a method of examining a diabetic complication with the marker as an indicator; and the like.

BACKGROUND ART

The bioaccumulation amounts of AGEs (Advanced Glycation End-products) which are various advanced glycation end products generated due to reactions between proteins and reducing sugars are well known to be particularly increased due to lifestyle-related diseases (Non Patent Literature 1).

Among them, $N^\varepsilon$(carboxymethyl)lysine (carboxymethyllysine, CML) has been reported as a principal antigenic AGEs structure generated from glucose, is easily measured, and has therefore received attention as a target for drug discovery since the 1990s (Non Patent Literature 2).

As described above, attempts have been continuously made to measure various AGEs structures including CML with AGEs-specific monoclonal antibodies (Non Patent Literature 3) or liquid chromatography triple quadrupole mass spectroscopes (LC-MS/MS), to specify AGEs structures involved in lifestyle-related diseases. However, any AGEs structure with significantly great variation in content in the living body with diabetes mellitus has not been found.

Takeuchi et al. (Patent Literature 1) immunized a fructose-modified protein to obtain an anti-AGEs antibody and described that an antigen recognized by the antibody is increased due to diabetes mellitus; however, the AGEs structure of the antigen has been unknown, and the antibody has not yet been in practical use.

As other examples of diabetes mellitus markers, hemoglobin A1c(HbA1c) has been known as a marker for variations in blood glucose in past 1 to 2 months, and glycated albumin has been known as a marker for variations in blood glucose in past 2 to 3 weeks. However, both the two markers do not become markers for complications of diabetes mellitus although becoming markers for variations in blood glucose in diabetes mellitus.

In contrast, although glucoselysine has a known structure, quantitative changes in glucoselysine for medical conditions have not been examined.

CITATION LIST

Patent Literature

[Patent Literature 1] Japanese Patent Laid-Open No. 2004-323515

Non Patent Literature

[Non Patent Literature 1] Nagai R, Shirakawa J, Fujiwara Y, Ohno R, Moroishi N, Sakata N, Nagai M. Detection of AGEs as markers for carbohydrate metabolism and protein denaturation. J Clin Biochem Nutr. 55(1):1-6, 2014

[Non Patent Literature 2] Reddy S, Bichler J, Wells-Knecht K J, Thorpe S R, Baynes J W. N epsilon-(carboxymethyl) lysine is a dominant advanced glycation end product (AGE) antigen in tissue proteins. Biochemistry. 34(34): 10872-10878, 1995

[Non Patent Literature 3] Nagai R, Shirakawa J I, Ohno R I, Hatano K, Sugawa H, Arakawa S, Ichimaru K, Kinoshita S, Sakata N, Nagai M. Antibody-based detection of advanced glycation end-products: promises vs. limitations. Glycoconj J. 33(4):545-552, 2016

SUMMARY OF INVENTION

As described above, AGEs which are advanced glycation end products have been previously suggested to be related to diabetes mellitus and complications thereof. However, such AGEs have not become practical clinical markers on a research level. The reasons thereof are because, although various AGEs are present in the living body, (1) it is difficult to measure the AGEs, and (2) any AGEs significantly increased due to diabetic complications in comparison with normal conditions have not been found.

For example, the structures of AGEs, such as CML, which are relatively easily measured, have received attention as targets for drug discovery since the 1990s. However, any components sufficiently exhibiting effects in the living body and being in practical use have not yet been found. The reason thereof is because AGEs which do not have structures in which the AGEs are significantly increased in medical conditions although being easily measured have been used as markers to be explored.

Examples of markers for diabetes mellitus (variations in blood glucose) include HbA1c and glycated albumin, which have been already measured on a worldwide level. However, any marker for complications thereof has not yet existed.

The present invention was made under the above-described circumstances in the conventional technology, with an objective to provide a marker that enables a diabetic complication to be examined.

The inventors studied intensively to solve the above-described problems. As a result, a substance that is increased in diabetic rats in comparison with normal rats was analyzed by a liquid chromatography triple quadrupole mass spectroscope (LC-MS/MS), the structure of glucoselysine which can be utilized as a marker for diabetic complications was specified, and the present invention was thus accomplished.

Any AGEs structures with great variations in the contents of AGEs in the living body with diabetes mellitus, other than the structure of the marker of the present invention, do not exist in the world.

Although the structure per se is not novel, the structure has not been reported to be measured as a marker for medical conditions such as diabetes mellitus. Glucoselysine is confirmed to be significantly increased due to cataract which is one of diabetic complications, and is therefore effective as a marker that enables the presence or absence of diabetic complications to be evaluated at a high probability.

In other words, the present invention relates to the following.

[1] A marker for examining a diabetic complication, including a compound represented by the following Formula (1), or a salt thereof.

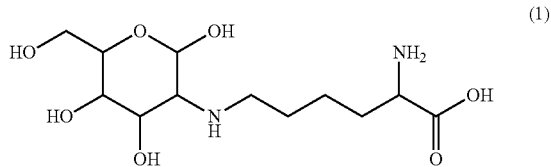 [SMILES: NC(CCCCNC1C(O)OC(CO)C(O)C1O)C(=O)O]

[2] The marker for examining a diabetic complication according to [1], wherein the compound represented by Formula (1) is a compound represented by the following Formula (1a) or (1b).

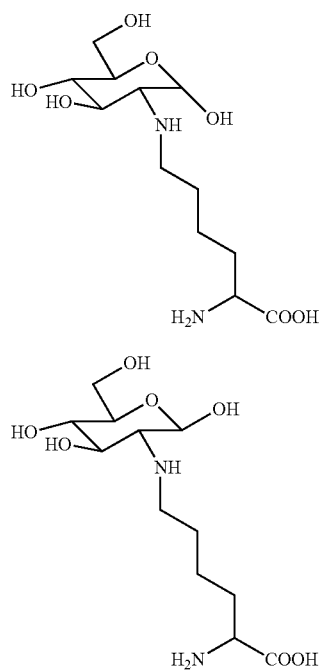

[3] A method of examining a diabetic complication with an amount of the marker according to [1] or [2] as an indicator, the method including:
(A) a step of measuring the amount of the marker according to [1] or [2] in a sample collected from a test subject; and
(B) a step of determining presence or absence, or a risk of development of the diabetic complication based on a result of measurement of the amount of the marker, obtained in the step (A).

[4] The method of examining a diabetic complication according to [3], wherein the sample is subjected to treatment with an acid such as hydrochloric acid in a liquid phase, and wherein the sample subjected to the treatment in the liquid phase is added to a strongly acidic cation exchange resin and subjected to elution under a nonacidic condition.

[5] The method of examining a diabetic complication according to [4], wherein the treatment in the liquid phase is treatment at 65 to 100° C. for 6 to 24 hours.

[6] The method of examining a diabetic complication according to any one of [4] to [5], the method further comprising performing filtration treatment of an eluate obtained by the elution from the strongly acidic cation exchange resin.

[7] The method of examining a diabetic complication according to any one of [3] to [6], wherein the measurement of the amount of the marker comprises liquid chromatography-mass spectrometry.

[8] The method of examining a diabetic complication according to [7], wherein the liquid chromatography-mass spectrometry is liquid chromatography-tandem mass spectrometry.

[9] Use of a compound represented by Formula (1), or a salt thereof, as a marker for examining a diabetic complication.

[10] A reagent for examining a diabetic complication, with which a compound represented by Formula (1), or a salt thereof is detected.

[11] Use of a compound represented by Formula (1), or a salt thereof, in producing a reagent for examining a diabetic complication, with which the compound represented by Formula (1), or the salt thereof is detected.

[12] A method of treating a diabetic complication, the method comprising:
examining a diabetic complication by the method of examining a diabetic complication according to any one of [3] to [8]; and
administering a therapeutic agent for a diabetic complication to a patient determined to have a diabetic complication.

The marker of the present invention is useful as a marker for examining a diabetic complication.

The current number of patients with diabetes mellitus which is one of lifestyle-related diseases in Japan, including incipient diabetics, climbs to 20.5 million, and there is an urgent social problem that such diabetes mellitus causes a decrease in QOL and an increase in total national medical expenditure.

Various complications such as retinopathy, cataract, nephropathy, and neurosis are developed around 5 to 10 years after the onset of diabetes mellitus.

However, any markers for complications have not existed although markers for blood glucose levels have existed until now. The markers for diabetic complications lead to early detection of the diabetic complications, further result in development of drugs for preventing the complications (such as chemical compounds, foods, and components derived from foods), and are therefore greatly considered to be likely to be measured on a worldwide level, as in the case of HbA1c.

DESCRIPTION OF EMBODIMENTS

Figure 1:
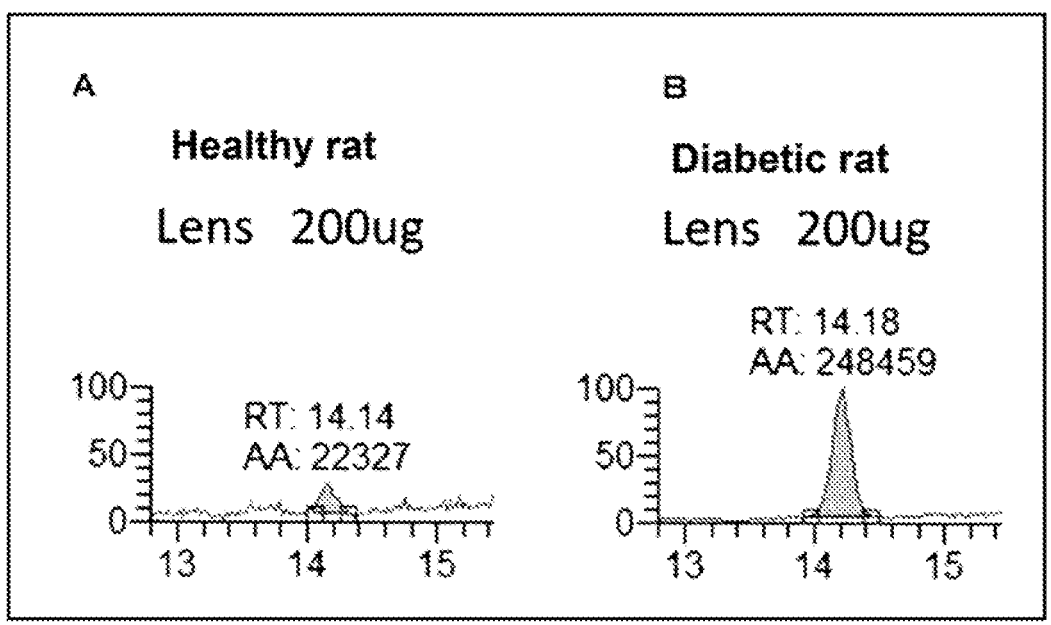
FIG. 1 is a diagram illustrating the results of measurement of a substance increasingly accumulated in the lenses of rats inducing diabetes mellitus in comparison with normal rats by LC-MS/MS analysis. A is a diagram illustrating the results of the measurement of the normal rats. B is a diagram illustrating the results of the measurement of the diabetic rats.

The present invention will be described below.

(Marker for Examining Diabetic Complications)

As a result of isolating a substance increasingly accumulated in the lenses of rats inducing diabetes mellitus in comparison with normal rats and of identifying the structure of the substance by LC-MS/MS analysis and NMR, the present inventors found the structure possessed by glucoselysine.

The compound having the structure was also detected in the serum of the rats inducing diabetes mellitus. In other words, the present inventors specified AGEs of which the structures have been unknown and which have been difficult to measure until then, and found the structures of the AGEs significantly varying due to a medical condition.

Measurement of blood glucoselysine by LC-MS/MS is more likely to enable evaluation of progression of a complication of diabetes mellitus, which has been previously impossible. A monoclonal or polyclonal antibody against glucoselysine enables the concentration of glucoselysine in the living body to be more easily evaluated.

The compound identified as a marker for examining a diabetic complication by the present inventors is glucoselysine having the following structure, and the chemical name of the compound is 2-amino-6-((2,4,5-trihydroxy-6-(hydroxymethyl)tetrahydro-2H-pyran-3-yl)amino)hexanoic acid.

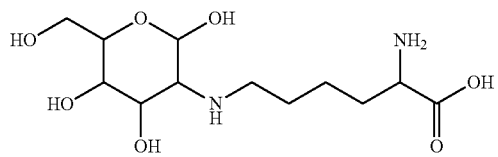
(1)

The compound which is the marker for examining a diabetic complication of the present invention (hereinafter may be simply referred to as "marker of the present invention") is preferably a compound which is α-glucoselysine having the following structure and physical properties and of which the chemical formula name is 2-amino-6-((2S,3R,4R,5S,6R)-2,4,5-trihydroxy-6-(hydroxymethyl)tetrahydro-2H-pyran-3-yl)amino)hexanoic acid, and a compound which is β-glucoselysine having the following structure and physical properties and of which the chemical formula name is 2-amino-6-(((2R,3R,4R,5S,6R)-2,4,5-trihydroxy-6-(hydroxymethyl)tetrahydro-2H-pyran-3-yl)amino)hexanoic acid.

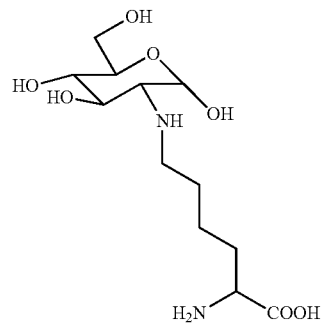
(1a)

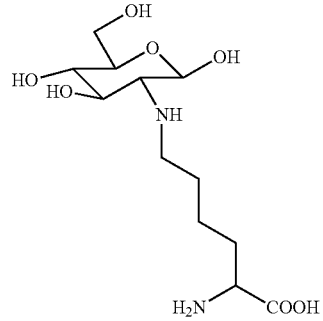
(1b)

Examples of salts of the compound (1) include physiologically acceptable salts. Examples of the physiologically acceptable salts include salts of alkali metals such as sodium and potassium; salts of alkali earth metals such as magnesium; and salts of amines such as ammonia, ethanolamine, and 2-amino-2-methyl-1-propanol. In addition, the kinds of the salts are not particularly limited as long as the salts are physiologically acceptable.

"Marker for examining diabetic complication" can be used as an indicator for determining the presence or absence, or risk of development of diabetic complications (of which examples include, but are not limited to, nephropathy, eye diseases, cardiovascular complications, neurosis, and the like, associated with diabetes mellitus). The marker can also be used for determining and diagnosing the presence or absence, or risk of development of the diabetic complications, for providing information therefor, and for developing methods for preventing or treating the symptoms and diseases of the diabetic complications.

Such diabetic complications are classified roughly into microangiopathy (microvascular disease) and macroangiopathy (arteriosclerotic disease), the former can be prevented in glycemic control, and therefore, it is desirable that it is possible to diagnose the microangiopathy at an early stage. Typical examples of the microangiopathy include diabetic neuropathy, diabetic retinopathy, and diabetic nephropathy, which are also referred to as the three major complications of diabetes mellitus. When diabetes mellitus is allowed to be unaddressed, neuropathy primarily occurs at a high rate at an early stage at which a complication occurs, and the progression of simple retinopathy is then observed. Then, microalbuminuria and intermittent proteinuria are observed, and aggravation such as vision loss or renal failure occurs. The marker for examination of the present invention can foresee the overall complications of diabetes mellitus and is a marker reflecting ocular abnormality as described in Examples mentioned later, and therefore, the marker can be preferably used as a marker for foreseeing the progression of retinopathy. Since the progression of retinopathy can be foreseen, the marker can be used for foreseeing the progression of, e.g., a complication such as subsequently occurring nephropathy as one aspect of the present invention.

"Marker for examining diabetic complication" of the present invention can also be used as "marker for examining diabetes mellitus", and such an embodiment is also included in the present invention.

(Method of Examining Diabetic Complication)

The present invention relates to a method of examining a diabetic complication (hereinafter may be simply referred to as "examination method of the present invention") with the amount of the marker of the present invention as an indicator. The examination method of the present invention comprises at least the following steps:

(A) the step of measuring the amount of the marker of the present invention in a sample collected from a test subject; and (B) the step of determining the presence or absence, or risk of development of a diabetic complication on the basis of the result of measurement of the amount of the marker, obtained in the step (A).

In the step (A), the amount (concentration, value corresponding to concentration, or the like) of the marker of the present invention in the sample collected from the test subject is measured.

Examples of the test subject in the examination method of the present invention include humans or mammals other than the humans desiring examination of a diabetic complication (or desired to be subjected to examination).

The biological sample used in the examination method of the present invention is a sample collected from a test subject desiring examination of a diabetic complication (or desired to be subjected to examination). Examples of the biological sample include any cells, tissues, and body fluids collected from the living body, for example, skin, muscle, bone, adipose tissue, cranial nervous systems, sense organs, circulatory systems such as heart and vessel, lung, liver, spleen, pancreas, kidney, digestive systems, thymus, lymph, blood, whole blood, serum, plasma, lymph fluid, saliva, urine, ascitic fluid, sputum, and the like, and cultures thereof. Among them, whole blood, serum, plasma, and urine are preferred, and serum and plasma are more preferred. The biological sample can be prepared and treated based on a usual method according to a subsequent measurement method. For example, a method of treating the sample preferably comprises: subjecting the sample to treatment with an acid such as hydrochloric acid in a liquid phase; and adding the sample subjected to the treatment in the liquid phase to a strongly acidic cation exchange resin and subjecting the sample to elution under a nonacidic condition.

It is further preferable that the treatment in the liquid phase is treatment at 65 to 100° C. for 6 to 24 hours.

It is further preferable to perform filtration treatment of an eluate obtained by the elution from the strongly acidic cation exchange resin.

A method of measuring the amount of the marker is not particularly limited. Examples of the measurement method include a capillary electrophoresis-mass spectrometry (CE-MS) method, high performance liquid chromatography (HPLC), gas chromatography (GC), chip LC, chip CE, a GC-MS method in which mass spectrometer (MS) is combined therewith, a liquid chromatography-mass spectrometry (LC-MS) method, a liquid chromatography-tandem mass spectrometry method such as an LC-MS/MS method or an LC-MS/MS/MS method, a CE-MS method, a time of flight mass spectrometry ((Q)TOF-MS) method, an independent MS method, an NMR method, and immunoassay by an ELISA assay or the like using an antibody. Preferred examples of the measurement method include an LC-MS method, an LC-MS/MS method, and an LC-MS/MS/MS method. The measurement can be performed based on the usual method of each measurement method except that a target for measurement is the marker of the present invention.

In the step (B), the presence or absence, or risk of development of a diabetic complication is determined based on the result of the measurement of the amount of the marker obtained in the step (A).

A reference or cutoff value used in the determination can be determined as appropriate in consideration of the kind and state of a sample used, a target for examination, required precision (reliability), and the like. For example, in the case of determining the presence or absence of development of a diabetic complication, the amount of the blood marker of a subject developing no diabetic complication is measured to determine a reference value in advance. When the amount of the blood marker of a test subject indicates a significant difference from the reference value, development of a diabetic complication can be determined. For example, in the case of determining the risk of development of a diabetic complication, the amount of the blood marker of a subject developing no diabetic complication is measured to determine a reference value, and the amount of the blood marker of a subject developing the diabetic complication is further measured to determine a reference value. Numerical values between the reference values are divided into several stages, and determination references such as, for example, "high risk of developing diabetic complication", "moderate risk of developing diabetic complication", and "low risk of developing diabetic complication" are determined according to each stage. The risk of developing a diabetic complication can be determined according to the amount of the blood marker of the test subject.

The examination method of the present invention may be a method of measuring the amount of the compound (1a) or (1b) described above, and is preferably a method of measuring the compounds (1a) and (1b), i.e., the compound (1). Examples of a reagent for examining a diabetic complication, with which the compound represented by Formula (1), or a salt thereof is detected, include antibodies.

EXAMPLES

The details of the present invention will be described with reference to Examples, but the present invention is not limited to the following Examples.

Example 1

(Detection of Glucoselysine in Living Body (Rat) by LC-MS/MS)

As a result of isolating a substance increasingly accumulated in the lenses of rats inducing diabetes mellitus in comparison with normal rats and of identifying the structure of the substance by LC-MS/MS analysis (results are illustrated in FIG. 1) and $^1$H-NMR, the structure possessed by glucoselysine having the following structure and physical properties was found.

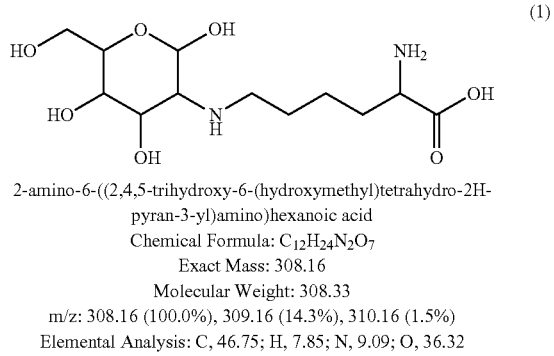 [SMILES: NC(CCCCNC1C(O)OC(CO)C(O)C1O)C(=O)O]

2-amino-6-((2,4,5-trihydroxy-6-(hydroxymethyl)tetrahydro-2H-pyran-3-yl)amino)hexanoic acid
Chemical Formula: $C_{12}H_{24}N_2O_7$
Exact Mass: 308.16
Molecular Weight: 308.33
m/z: 308.16 (100.0%), 309.16 (14.3%), 310.16 (1.5%)
Elemental Analysis: C, 46.75; H, 7.85; N, 9.09; O, 36.32

Glucoselysine in the living body was analyzed by LC-MS/MS.

In other words, 1 mL of 6 N iron-free hydrochloric acid was added to 200 μg of liquid in which the lens of each of normal rats and diabetes mellitus model rats (N=5) was disrupted, and the resultant was heated at 100° C. for 18 hours and subjected to hydrolysis. After the hydrolysis, the sample evaporated to dryness by centrifugal concentration was dissolved in 1 mL of distilled water and fractionated using a Strata-X-C column (Phenomenex, Torrance, CA, USA) as a cation-exchange column.

The column was washed with 1 mL of MeOH and then equilibrated with 1 mL of distilled water, and a total amount of the sample was then passed, washed with 3 mL of 2% formic acid, and eluted with 3 mL of 7% ammonia. The eluted fraction was evaporated to dryness, dissolved in 1 mL of 20% acetonitrile comprising 0.1% formic acid, and measured by LC-MS/MS (TSQ Quantiva, Thermo Fisher).

A ZIC (registered trademark)-HILIC column (150×2.1 mm, 5 μm)(Merck Millipore, Billerica, MA, USA) was used as the column for LC-MS/MS, and a mobile phase was allowed to be gradient with distilled water containing 0.1% formic acid and acetonitrile containing 0.1% formic acid. Ionization was performed by an electrospray ionization method in a positive mode, glucoselysine was measured with precursor ion m/z 309 and product ion m/z 291 (collision energy of 12 V), and $[^{13}C_6]$glucoselysine as an internal standard was measured with precursor ion m/z 315 and product ion m/z 297.

Both the elution positions of glucoselysine and the internal standard are around 14 min.

Figure 2:
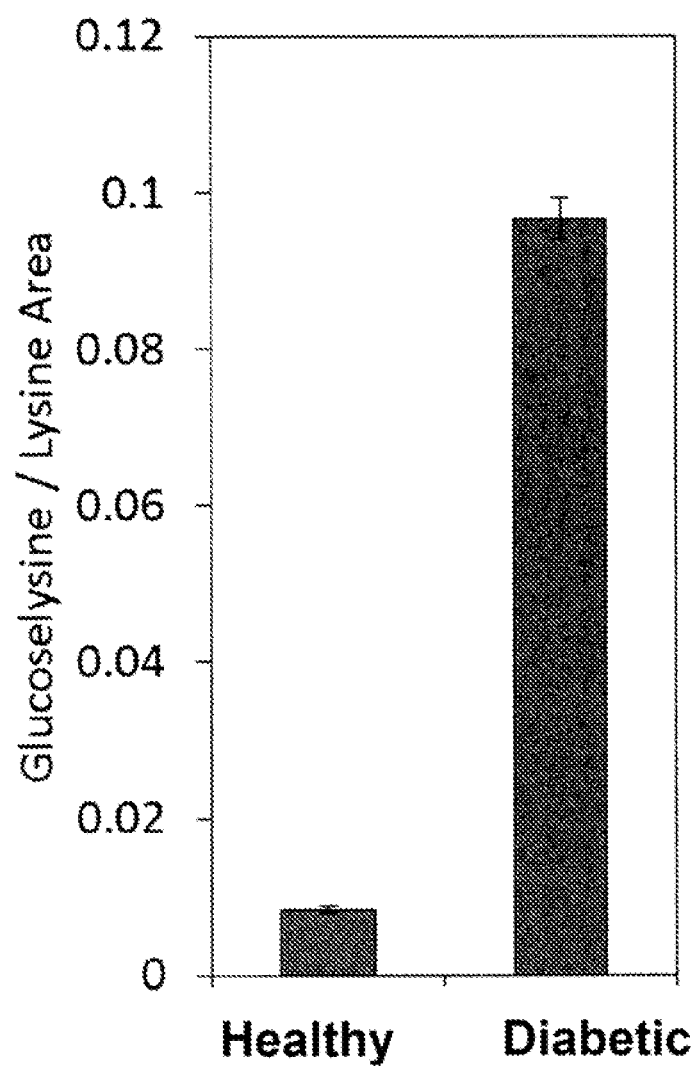
FIG. 2 is a diagram illustrating the results of measurement of glucoselysine in the living bodies (in the lenses of the normal and diabetes mellitus model rats) using LC-MS/MS.

The results are illustrated as area ratios between glucoselysine and lysine in a chart. The results are illustrated in FIG. 2. Glucoselysine in the lenses of the diabetes mellitus model rats with respect to the normal mice was shown to be significantly increased.

Example 2

(Detection of Glucoselysine in Living Body (Rat) with Antibodies)

The contents of glucoselysine and CML in the lens of each of normal rats and diabetes mellitus model rats (N=5) were measured using an antibody recognizing glucoselysine and a CML antibody (anti-CML antibody clone 6D12, Cosmo Bio Co., Ltd.).

Figure 3:
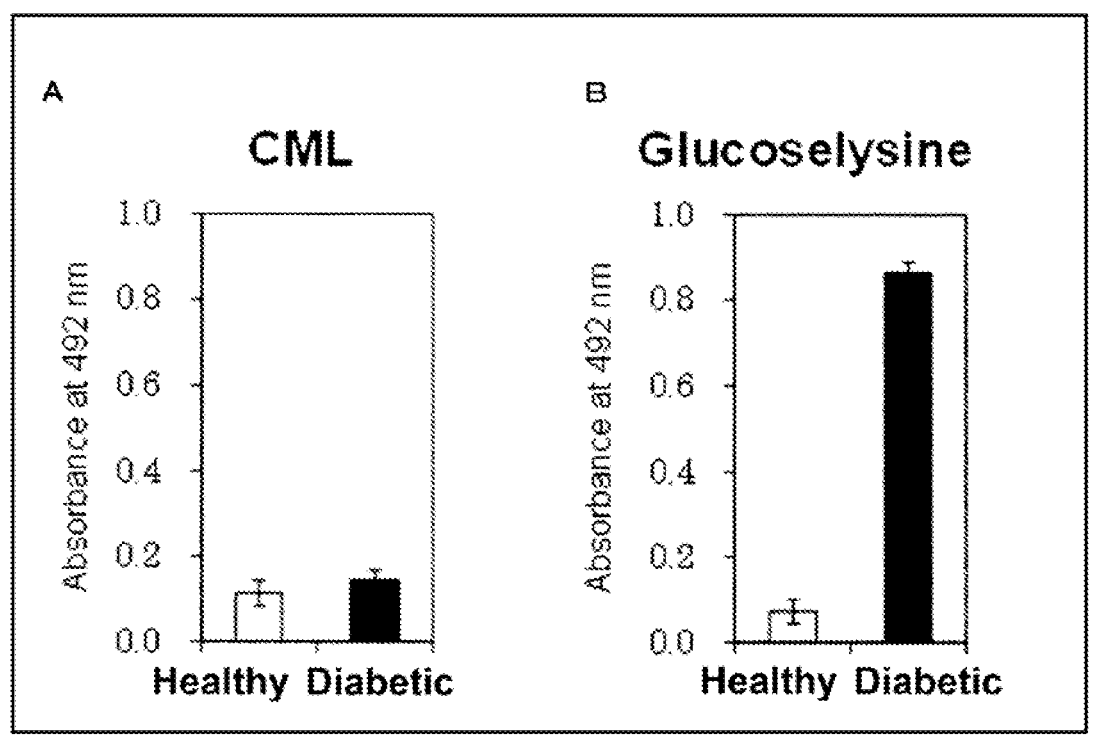
FIG. 3 is a diagram illustrating the results of measurement of glucoselysine in the lenses of the normal and diabetes mellitus model rats using antibodies. A is a diagram illustrating the results of the measurement of CML in the lenses of the rats using a CML antibody. B is a diagram illustrating the results of the measurement of glucoselysine in the lenses of the rats using an antibody recognizing glucoselysine.

The results are illustrated in FIG. 3. There was no significant difference between the amounts of CML in the lenses of the normal mice and the diabetes mellitus model rats. In contrast, there was a significant difference between the amounts of glucoselysine in the lenses of the normal mice and the diabetes mellitus model rats.

It became clear that glucoselysine is significantly increased due to development of diabetes mellitus and complications thereof in detection of glucoselysine using a biological sample.

Example 3

(Detection of Glucoselysine in Living Body (Mouse) by LC-MS/MS)

Glucoselysine in the lenses of normal mice (N=12) and diabetes mellitus model mice (N=20) was detected based on the technique of Example 1.

Figure 4:
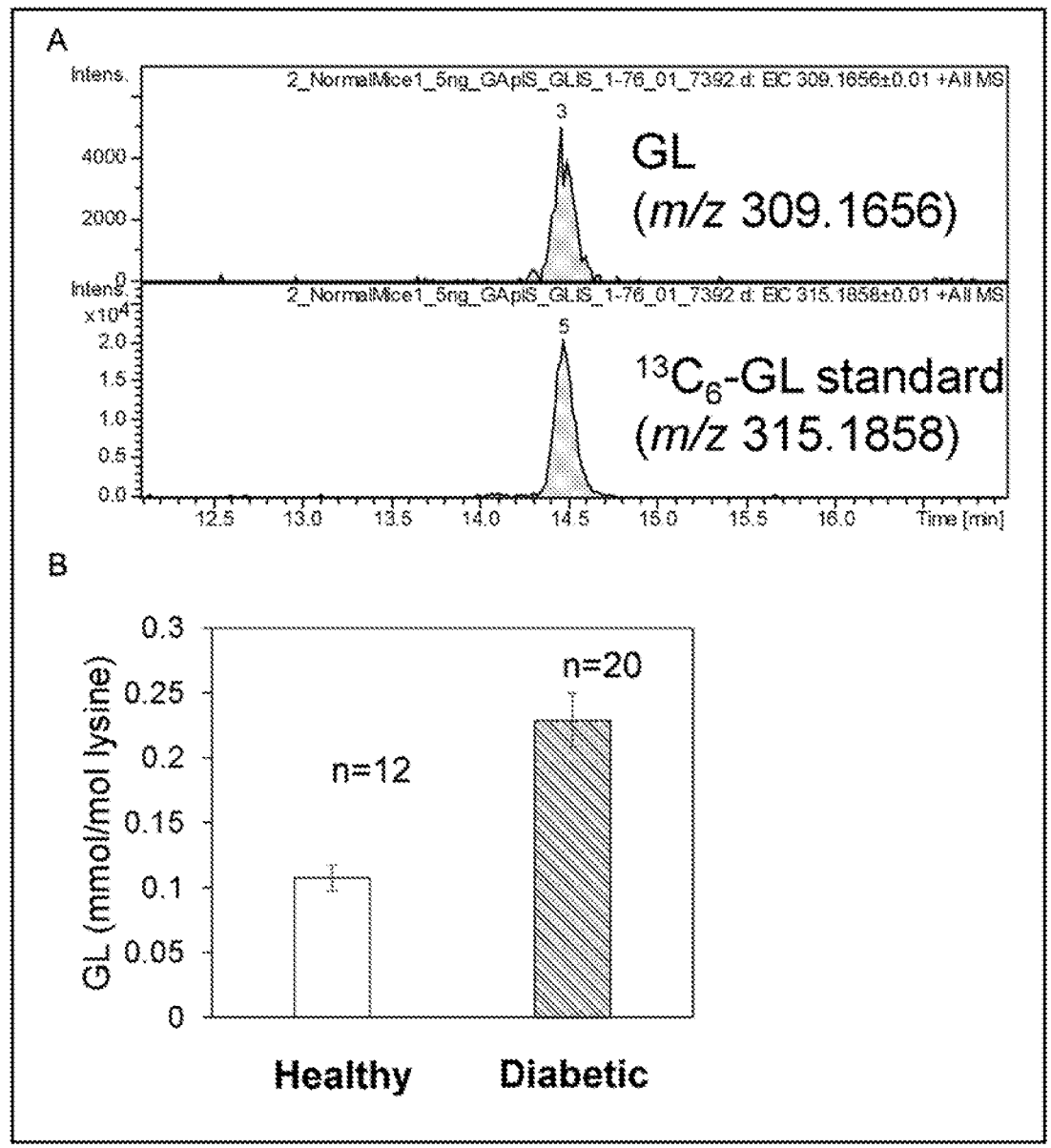
FIG. 4 is a diagram illustrating showing the results of measurement of glucoselysine (GL) in the lenses of normal and diabetes mellitus model mice. A is a diagram illustrating the results (upper section: GL; and lower section: internal standard) of the measurement of GL in the lenses of the normal mice. B is a diagram illustrating the results of the measurement of the normal and diabetes mellitus model mice.

The results are illustrated in FIG. 4. Both the elution positions of glucoselysine and the internal standard are around 14 min (A of FIG. 4). Glucoselysine in the lenses of the diabetes mellitus model mice with respect to the normal mice was shown to be significantly increased (B of FIG. 4).

Example 4

(Evaluation of Stability of Glucoselysine)

Glucoselysine and fructoselysine were synthesized by reaction between fructose and lysine and by reaction between glucose and lysine, respectively, and were isolated by HPLC. Hydrochloric acid hydrolysis of each of glucoselysine and fructoselysine was performed based on the technique of Example 1 except that a treatment time period was changed. After the hydrochloric acid hydrolysis, a substance included in a sample in each aliquot treatment time period was identified by QTOF-MS (Bruker, compact).

Figure 5:
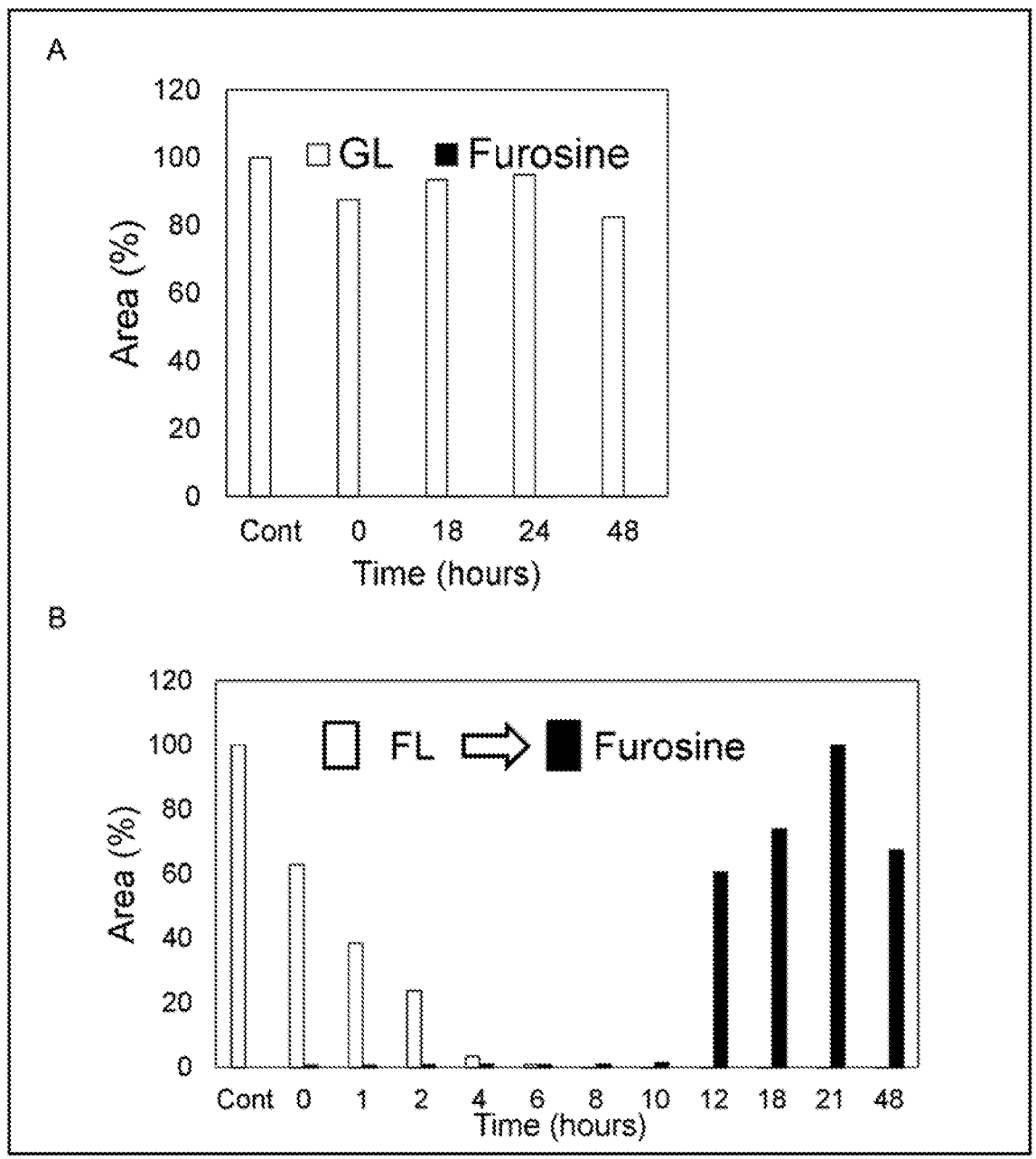
FIG. 5 is a diagram illustrating the results of tests for stability against hydrochloric acid hydrolysis of glucoselysine (GL) and fructoselysine (FL). A is a diagram illustrating the test results of GL. B is a diagram illustrating the measurement results of FL.

The results are illustrated in FIG. 5. Fructoselysine is an isomer of glucoselysine. Like glucoselysine, fructoselysine was confirmed to be increased in the lenses of the diabetes mellitus model mice. However, it was impossible to detect fructoselysine 6 hours after the hydrochloric acid hydrolysis treatment. Fructoselysine was converted into furosine by the hydrochloric acid hydrolysis, and furosine was detected 12 hours after the hydrochloric acid hydrolysis treatment. In contrast, glucoselysine was not converted into furosine but was able to be quantified even 18 hours after the hydrochloric acid hydrolysis treatment. It became clear that glucoselysine is stable against hydrochloric acid hydrolysis.

Example 5

(Detection of Glucoselysine in Living Body (Human) by TOF-MS)

Blood was collected from normal persons (N=3) and diabetic patients (N=11) to prepare serum, and glucoselysine in the serum was analyzed by QTOF-MS.

Figure 6:
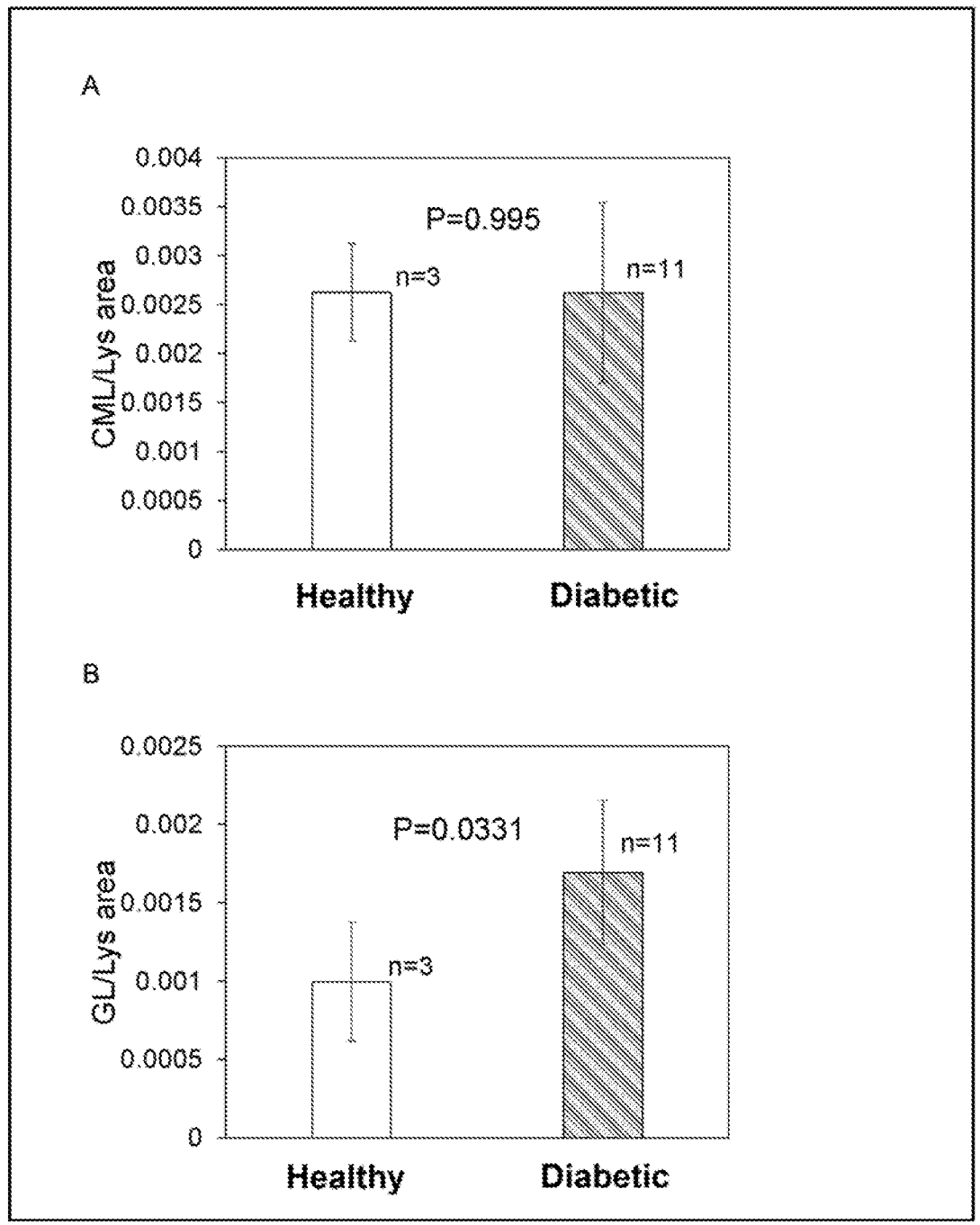
FIG. 6 is a diagram illustrating the results of measurement of CML and glucoselysine (GL) in the serum of normal and diabetic patients using TOF-MS. A is a diagram illustrating the results of the measurement of CML. B is a diagram illustrating the results of the measurement of GL.

The results are illustrated in FIG. 6. There was no difference between the amounts of CML in the normal persons and the diabetic patients (A of FIG. 6). The amount of glucoselysine in the serum of the diabetic patients was shown to be significantly increased with respect to the normal persons (B of FIG. 6).

INDUSTRIAL APPLICABILITY

The present invention can be applied to a marker for examining diabetes mellitus and complications thereof, a supplement or food for suppressing diabetes mellitus and complications thereof, and the like.

What is claimed is:

1. A method of examining a diabetic complication, the method comprising:
(A) a step of measuring the amount of a compound represented by Formula (1a) or (1b) in a hydrolyzed sample that is a result of hydrolyzing a collected sample from a test subject, thereby obtaining a result of measurement of the amount of the compound

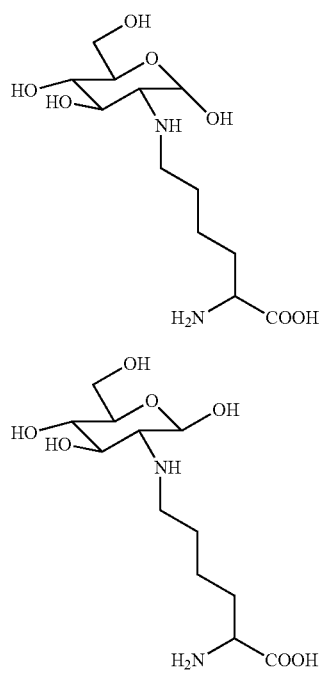

(B) a step of determining presence or a risk of development of the diabetic complication based on the result of measurement of the amount of the compound; and
(C) administering a therapeutic agent for a diabetic complication to the test subject.

2. The method of examining a diabetic complication according to claim 1, further comprising a step of treating the collected sample with an acid, wherein the step of treating the collected sample with an acid is performed in a liquid phase, and then subjecting the acid-treated sample to a strongly acidic cation exchange resin, before the step (A).

3. The method of examining a diabetic complication according to claim 2, wherein the step of treating the collected sample with an acid is performed at 65 to 100° C. for 6 to 24 hours.

4. The method of examining a diabetic complication according to claim 2, the method further comprising performing filtration treatment of an eluate obtained by elution from the strongly acidic cation exchange resin.

5. The method of examining a diabetic complication according to claim 1, wherein the measurement of the amount of the compound comprises liquid chromatography-mass spectrometry.

6. The method of examining a diabetic complication according to claim 5, wherein the liquid chromatography-mass spectrometry is liquid chromatography-tandem mass spectrometry.

7. The method of examining a diabetic complication according to claim 1, wherein the measurement of the amount of the compound comprises quadrupole time of flight mass spectrometry (QTOF-MS) method.

* * * * *